(12) United States Patent
Curradini

(10) Patent No.: US 7,374,575 B2
(45) Date of Patent: May 20, 2008

(54) FEMORAL STEM FOR HIP PROSTHESIS

(76) Inventor: Giorgio E. Curradini, Via Stampa, 8, Milano (IT) 20123

( * ) Notice: Subject to any disclaimer, the term of this patent is extended or adjusted under 35 U.S.C. 154(b) by 153 days.

(21) Appl. No.: 10/558,351

(22) PCT Filed: May 29, 2003

(86) PCT No.: PCT/IT03/00331

§ 371 (c)(1),
(2), (4) Date: Nov. 23, 2005

(87) PCT Pub. No.: WO2004/105653

PCT Pub. Date: Dec. 9, 2004

(65) Prior Publication Data

US 2006/0282171 A1     Dec. 14, 2006

(51) Int. Cl.
*A61F 2/42* (2006.01)
(52) U.S. Cl. .................. 623/22.11; 623/23.17
(58) Field of Classification Search ............ 623/23.31, 623/23.26, 23.29, 23.18, 23.35, 22.41, 23.15, 623/23.32, 23.44, 23.5, 22.42, 22.43
See application file for complete search history.

(56) References Cited

U.S. PATENT DOCUMENTS 5,002,575 A * 3/1991 Johnson ..................... 623/23.5
5,041,140 A * 8/1991 Teinturier ................. 623/22.17
5,755,811 A * 5/1998 Tanamal et al. ......... 623/23.35

FOREIGN PATENT DOCUMENTS

| DE | EP 0669116 | * | 8/1995 |
| DE | 4437479 | | 5/1996 |
| EP | 0354142 | | 2/1990 |
| EP | 0669116 | | 8/1995 |
| FR | EP 0354142 | * | 7/1989 |
| FR | 2660853 A | * | 10/1991 |
| FR | 2681239 | | 3/1993 |

* cited by examiner

*Primary Examiner*—Thomas J Sweet
*Assistant Examiner*—Jonathan R Stroud
(74) *Attorney, Agent, or Firm*—IP Strategies

(57) ABSTRACT

A femoral stem for hip prosthesis is disclosed comprising: a main body with a mainly longitudinal development and a generally wedge shaped, which is inserted into the femoral canal present in the body of the femur; a central body of a generally trapezoidal shape integral with the main body, located in the proximal zone of the femur; an appendix projecting from the central body provided with a terminal pin receiving spherical head of joint into the cotyle belonging to the prosthesis and inserted into the acetubular zone of the pelvic bone. The main body and the central body are defined by a shaped surface on one side and a mixtilinear surface on the opposite side from which a shaped notch is starting involving the central body and extending up to the proximity of the projecting appendix.

10 Claims, 6 Drawing Sheets

FEMORAL STEM FOR HIP PROSTHESIS

BACKGROUND OF THE INVENTION

The present invention relates to a femoral stem for hip prosthesis used for replacing the diseased natural joint of the hip with an artificial device taking its functions.

It is well known that in the orthopaedic field surgery of the hip joint is generally carried out for old people to treat pathologies such as arthrosis, arthritis or hip luxation generating a progressive wear of the hip joint.

It is well known that the hip joint connects the femur to the pelvis and comprises the femur head engaged in the acetabulum which is a joint cavity on the outer face of the pelvic bone.

In the femur in addition to said femoral head there are the neck connecting the head to the femoral body, having a rather longitudinal development, and a couple of protrusions, the greater and the lesser trochanter, arranged on opposite sides on the femoral body.

On the basis of the natural shape of the hip, the prosthesis to be implanted comprises therefore a femoral part called stem and made of metal, generally of a titanium alloy or stainless steel, inserted into a longitudinal cavity made in the femoral body and an acetabular part called cotyle which is applied into a seat made in the pelvis.

The cotyle is generally consisting of two parts, the first made of metal, titanium or its alloys, and the other facing the stem made of polyethylene of high molecular weight or ceramics.

The cotyle is coupled with a spherical head also made of metal or ceramics, which is fixed to the stem and is the pivot of the artificial joint.

More particularly the femoral stem comprises a main body known also as shaft which is inserted in the femur body. Such a shaft ends at the trochanter zone with a shoulder while continuous medially with a neck projecting from the shoulder to the cotyle of the prosthesis and having a terminal cone to which the above mentioned spherical head is applied.

The surgical operation to the patient's hip therefore consists in preparing in the acetabular zone of the pelvis using proper spherical mills, a seat in which the cotyle is then applied.

Then the neck is being cut with a saw, said operation being called resection or osteotomy and in the subsequent preparation through proper rasps, of the internal canal of the femoral bone where the prosthetic stem is then inserted.

Finally the spherical head is assembled with the femoral stem thus assembling the prosthesis and restoring the original configuration of the limb.

In this way once implanted, the femoral stem and the cotyle reproduce almost faithfully the original shape of the femur and the acetabulum respectively, replacing the diseased parts, allowing a pain relief and a recovery of the joint function so as to allow patient to have a normal life for many years.

The prosthesis is anchored to the bone through two main methods, the first consisting in solidification during surgery of a liquid polymer that in this way acts as a glue, connecting firmly the bone to the prosthesis. In this case a cemented prosthesis is obtained.

The prosthesis of most modern conception are however pressure applied into the bone, to which they are stably anchored through a natural process of bone integration occurring with time, enhanced also by the fact that the metal stem is rather sanded, that is has a rough outer surface, thus increasing the anchoring ability of the bone to the stem.

The present invention intends to address this second kind of prosthesis.

A wide variety of embodiments of femoral stems for hip prosthesis are presently available on the market, performing in different ways the object aimed to.

The main limitation of the femoral stems of the prior art consists in that they are rather rigid, above all in relation to the intrinsic elasticity characteristics of the bones of the human body and more particularly of the femur.

The application of a rigid metal body inside the femur generates indeed physical decompensations to the person, above all in their areas of greater load transmission such as the cortical medial areas which become therefore particularly critical areas.

The transmitted stresses are not properly absorbed by the cortical bone which is of the compact kind, with the consequence of causing pain to the person but more particularly causing degeneration or even progressive disappearance of the bone in the less stimulated zones, among which a particular place is to be given to the Calcar located immediately above the lesser trochanter.

Another limitation of the femoral stems of the prior art is their high dimension, more particularly at the shoulder, contributing to making the entire structure stiff.

The solution to make less cumbersome stems reducing the shoulder dimension, is not always possible because at this point the torsional stability of the prosthesis is strongly reduced.

Moreover post operative radiographs show for these constructional types a line of detachment between bone and prosthesis at the lateral shoulder of the stem.

It is clear that this aspect has a negative influence on the performance of the prosthetic implant because the stem results to be partially detached from the femur, not to speak of the clear troubles that this situation causes for the patient's health.

A further attempt to solve the problem of the stiffness of the prosthetic stem inside the femur is disclosed in the document EP 308297, wherein the stem has a notch of different shape made starting from the surface connecting the shoulder with the neck and developed downwards in the proximal zone.

Laboratory test of mechanical resistance show however that after having being subject to a set of load cycles, this femoral stem fails by fatigue at the notch end, where a critical section is generated caused by an excessive concentration of stress. In this connection it is to be recalled that there is a European regulation (UNI7206) according to which the femoral stem of hip prosthesis must withstand five millions load cycles to be approved.

A second drawback of the stem disclosed in said document is that during the load only the part facing the lesser trochanter bends downwards, while the shoulder remains stationary thus preventing to keep the greater trochanter reactive.

Another drawback of this stem is due by the fact that the notch as shaped allows that chips produced by rubbing of the spherical head against the cotyle, to deposit by gravity inside through the upper opening, this leading with time to prosthesis failure.

SUMMARY OF THE INVENTION

The present invention aims at overcoming the above mentioned drawbacks and limitations of the prior art.

More particularly it is a first object of the invention to provide a femoral stem for hip prosthesis that under low conditions allows to stress the femur in a more uniform way relative to equivalent stems of the prior art.

It is another object to provide the femoral stem that does not allow generation of sides for accumulation of particles and chips produced inside the joint.

Said objects are attained by a femoral stem for hip prosthesis that according to the contents of the main claim comprises:
- a main body with mainly longitudinal development and with a generally wedge shape, adapted to be inserted into the femoral canal of the femur body;
- a central body of a generally trapezoidal shape integral with said main body, adapted to be received in the proximal zone of said femur;
- an appendix projecting from said central body, provided with a terminal pin adapted to receive spherical join head in the cotyle belonging to said prosthesis and inserted in the acetabular zone of the pelvic bone,
- and wherein said main body and said central body are defined by a shaped surface on one side and a mixtilinear surface on the opposite side from which a shaped notch is starting, involving said central body and extending up to the proximity of said projecting appendix.

According to a preferred embodiment of the invention, the mixtilinear surface comprises a first generally straight surface belonging to the central body, and a second generally straight surface belonging to the main body, connected to the first surface through a generally convex radiused zone from which the shaped notch is starting.

Advantageously the femoral stem of the invention stimulates the femoral bone in a more uniform way relative to equivalent stems of the prior art.

More particularly, the femoral stem stimulates efficiently the femur area called the calcar, that otherwise is progressively but invariably degenerated, thus warranting the reactivity and consequently its life for a more extended period of time in comparison with the stems of the prior art.

This is not to the detriment of the greater trochanter of the femur, which is also stimulated because the entire central body bends downwards when the stem is loaded.

Still advantageously the femoral stem of the invention keeps a rather widened geometry enhancing to obtain an optimal primary stability, to be understood as the torsional resistance during the period immediately after the surgery.

Again advantageously the invention allows to reach an optimal secondary stability to be understood as the ability of the bone to integrate the femoral stem in the subsequent phases after the post operative course during the patient's normal life.

In advantageously way moreover the shaped notch realized to make the stem more subject to deformation and therefore compatible with the intrinsic characteristics of the femur, is developed upwards and therefore prevents the chips falling by gravity to be deposited inside it.

Moreover the shaped notch made at a discontinuity zone of one of the lateral surfaces defining the stem, namely where the inclination of the lateral profile of the stem is changing, divides the portion of the femoral stem anchored to the cortical bone from the portion anchored to the spongy bone.

This prevents that in proximity of the notch a stress is generated due to the point contact of the stem with the cortical bone.

BRIEF DESCRIPTION OF THE DRAWINGS

The foregoing objects and advantages, and others that will be pointed out in the course of the present description, will be better understood by the description of preferred embodiments of the invention given as illustrative but not limiting examples and shown in the accompanying sheets of drawings in which:

FIG. 1 shows the femoral bone generally indicated with F and its joint in the acetabular zone generally indicated with E, and belonging to the pelvic bone O to form the hip A.

DESCRIPTION OF THE INVENTION

One can also see the femoral body C, with straight development, the head T of femur F articulated in the acetabular zone E and connected to the femoral body C through the neck L, the lesser and greater trochanter indicated with P and G respectively, the proximal zone Z comprised between the two trochanters and the femoral canal N in the femoral body C in which the prosthetic stem is inserted.

In this connection it is adviseable to point out the internal structure of the femur F in which there is the spongy bone J and mainly located in the diaphises portion of the femur F.

One can also see in heavy lines, the osteotomy line M along which the head T of the femur F is being cut to allow to work the femoral canal N.

Figure 1:
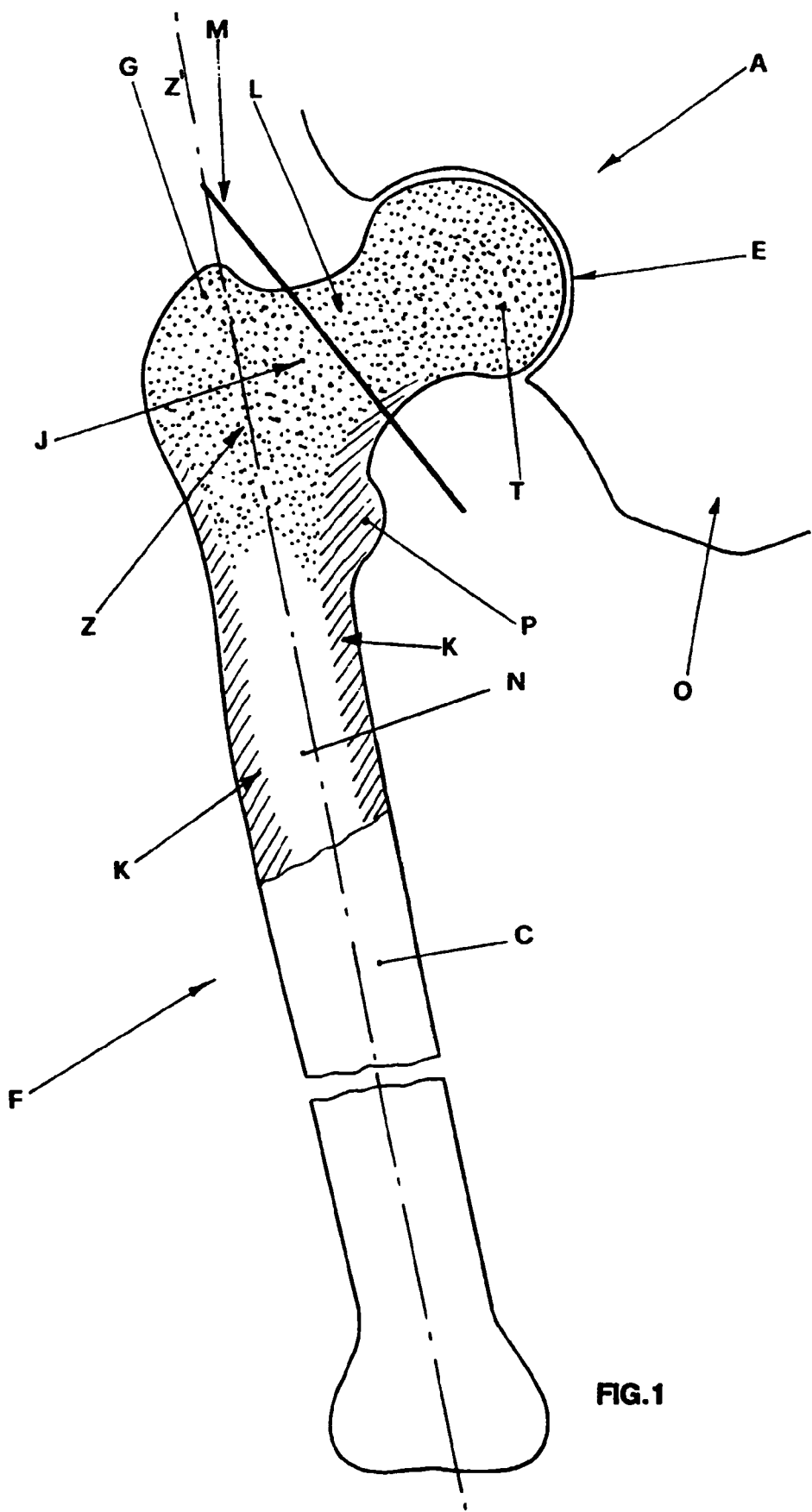
FIG. 1 is a partially sectioned view of the femoral bone and the hip joint.
Figure 2:
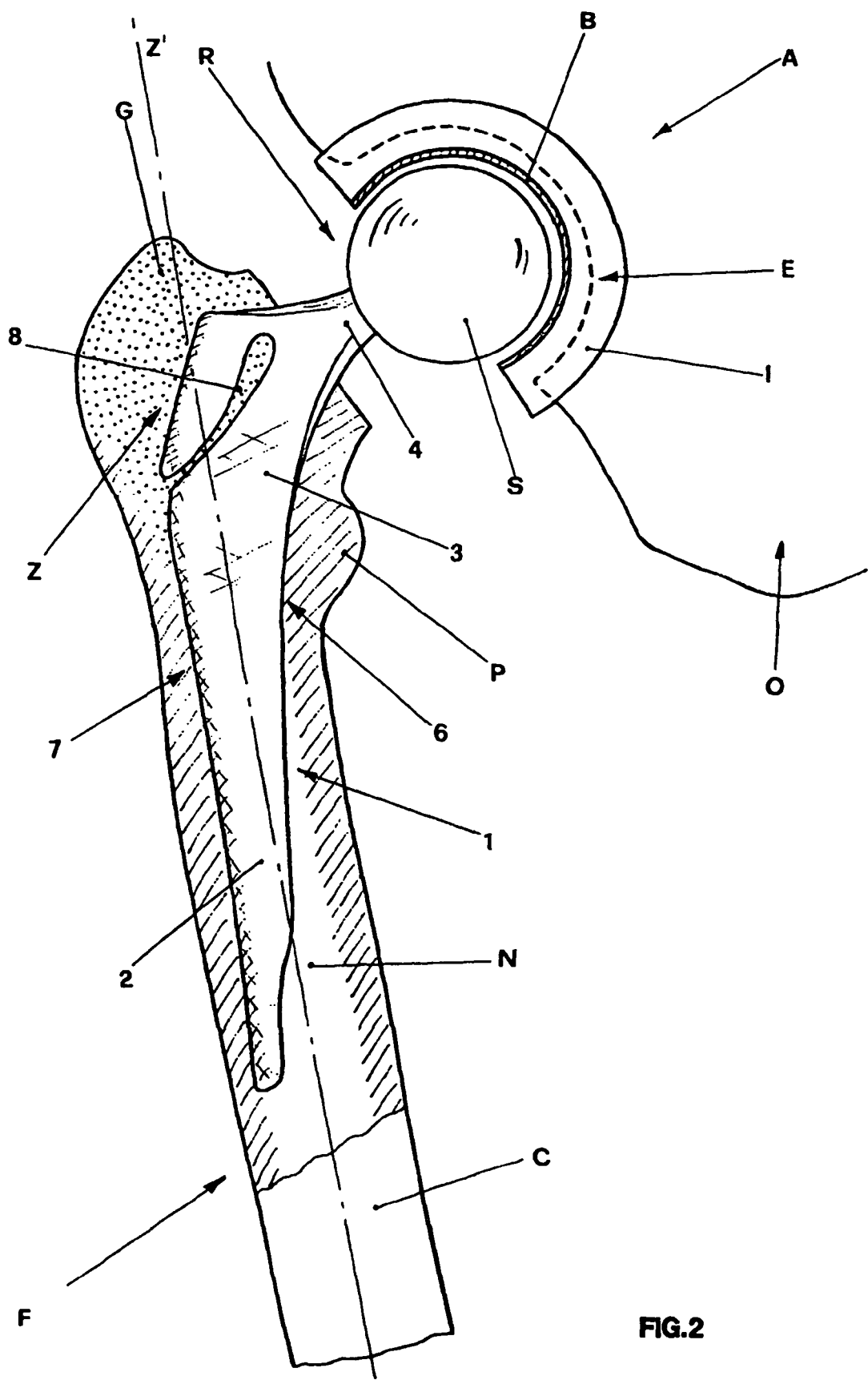
FIG. 2 is a partially sectioned of the femoral stem of the invention inserted in the femoral bone of FIG. 1.

In FIG. 2 the femoral stem of the invention generally indicated with 1 and belonging to prosthesis R, is shown in the applied condition, that is inserted inside the femur F.

One can see that the femoral stem 1, preferably but not necessarily made of titanium alloy, comprises a main body 2, with a mainly longitudinal development and with a generally wedge shape, which is inserted into the femoral canal N of the body C of femur F.

Therefore the femoral stem 1 comprises a central body 3 of a generally trapezoidal shape integral with the main body 2 which is located in the proximal zone Z of femur F.

Figure 3:
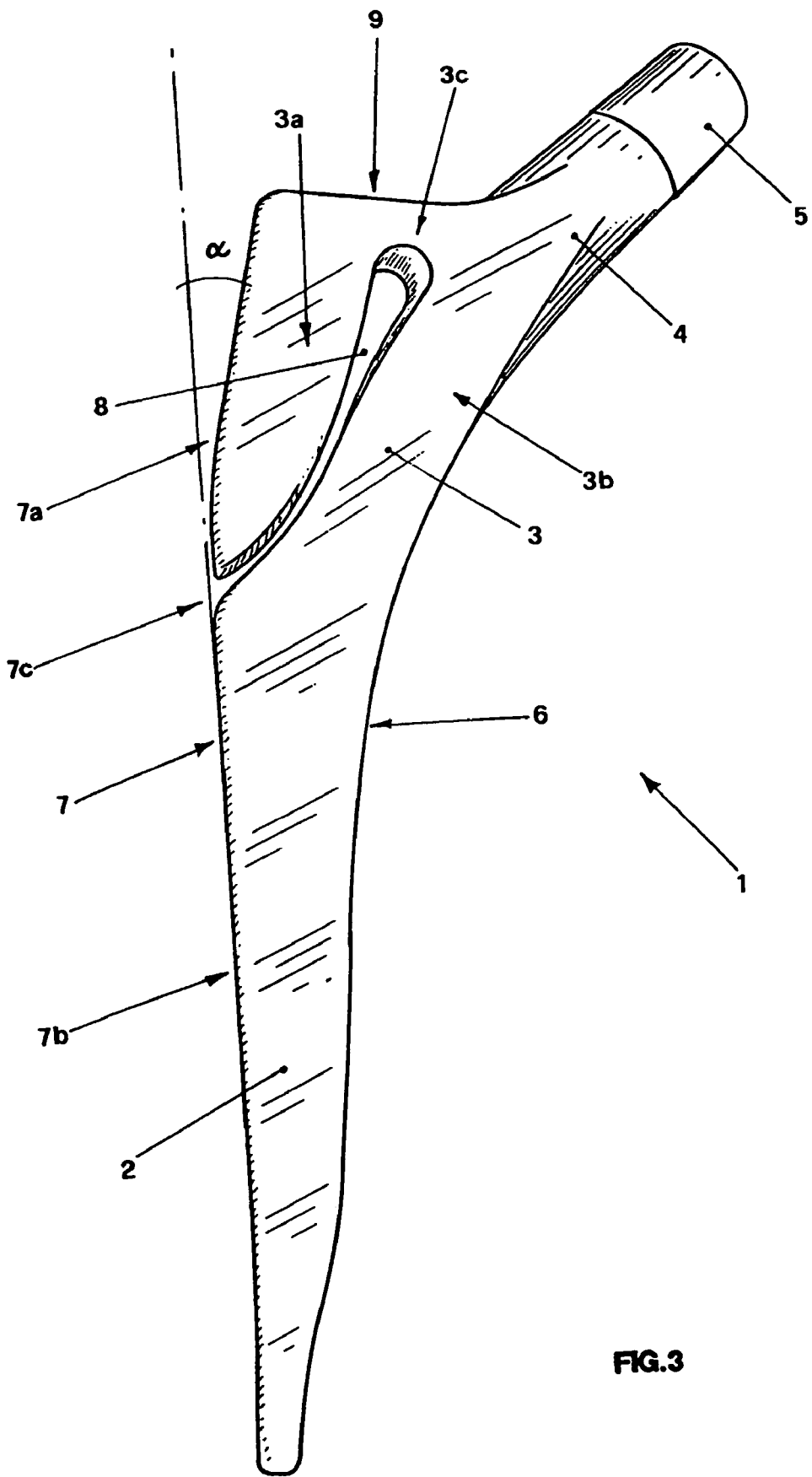
FIG. 3 is a view of the femoral stem of the invention.

Finally the femoral stem 1 comprises an appendix 4 projecting from the central body 3, provided with a terminal pin not visible in FIG. 2 but seen in FIG. 3 where it is indicated with 5, receiving the spherical head S of joint in the cotyle I belonging to the prosthesis R inserted in the acetabular zone E of the pelvic bone and provided with a portion B for instance made of polyethylene, metal or ceramics, facing the femoral stem 1.

According to the invention, the main body 2 and the central body 3 are defined by a shaped surface 6 on one side and a mixtilinear surface 7 on the other side, from which a shaped notch 8 is starting, involving the central body 3 and extending up to the proximity of the projecting appendix 4.

In the present embodiment the shaped surface 6 as a concave-convex profile in longitudinal section.

As shown in FIG. 3, the mixtilinear surface 7 consists of a generally straight first surface 7a belonging to the central body 3 and a second generally straight surface 7b belonging to the main body 2 connected to the first surface 7a through a generally convex radiused zone 7c from which the shaped notch 8 is starting.

Therefore at the radiused zone 7c a change of inclination of the profile of the femoral stem 1 occurs, so that the extension of the second surface 7b defines with the first surface 7a an acute angle $\alpha$.

Said change of inclination of the lateral profile of the femoral stem 1 at the connection zone between the main body 2 and the central body 3 is dictated by the dual requirement to obtain stem of a widened shape at the proximal zone Z to warrant a good torsional stability from one side, and to allow a saving in bone removal of femur F in the zone adjacent to the greater trochanter G from the other side to insert the femoral stem 1 inside the femur F.

In view of the various muscles present in said zone connected to the femur F such as for example those very important ones of the glutei, it is clear then the more one succeed to preserve this zone and the better will be the post operative recovery of the patient. This is obtained just by making a mixtilinear surface 7 as taught by the present invention.

Moreover the change of inclination of the lateral profile of the femoral stem 1 occurs at a zone that when the insertion of the femur F is completed, is generally located in contact with the spongy bone J of the femur which is more internal and almost exclusively present in the proximal zone Z. This allows to avoid that at the shaped notch 8 there is stress concentration that otherwise would occur if the notch would be in contact with the cortical bone K.

In FIG. 3 one can also see that the shaped notch 8 divides the central body 3 into a first zone 3a located generally facing the greater trochanter G of the femur F and a second zone 3b located generally facing the lesser trochanter P of the femur F.

The first zone 3a and the second zone 3b are mutually connected by a bridge 3c comprised between the shaped notch 8 and the radiused surface 9 between the projecting surface 4 and the mixtilinear surface 7.

Figure 4:
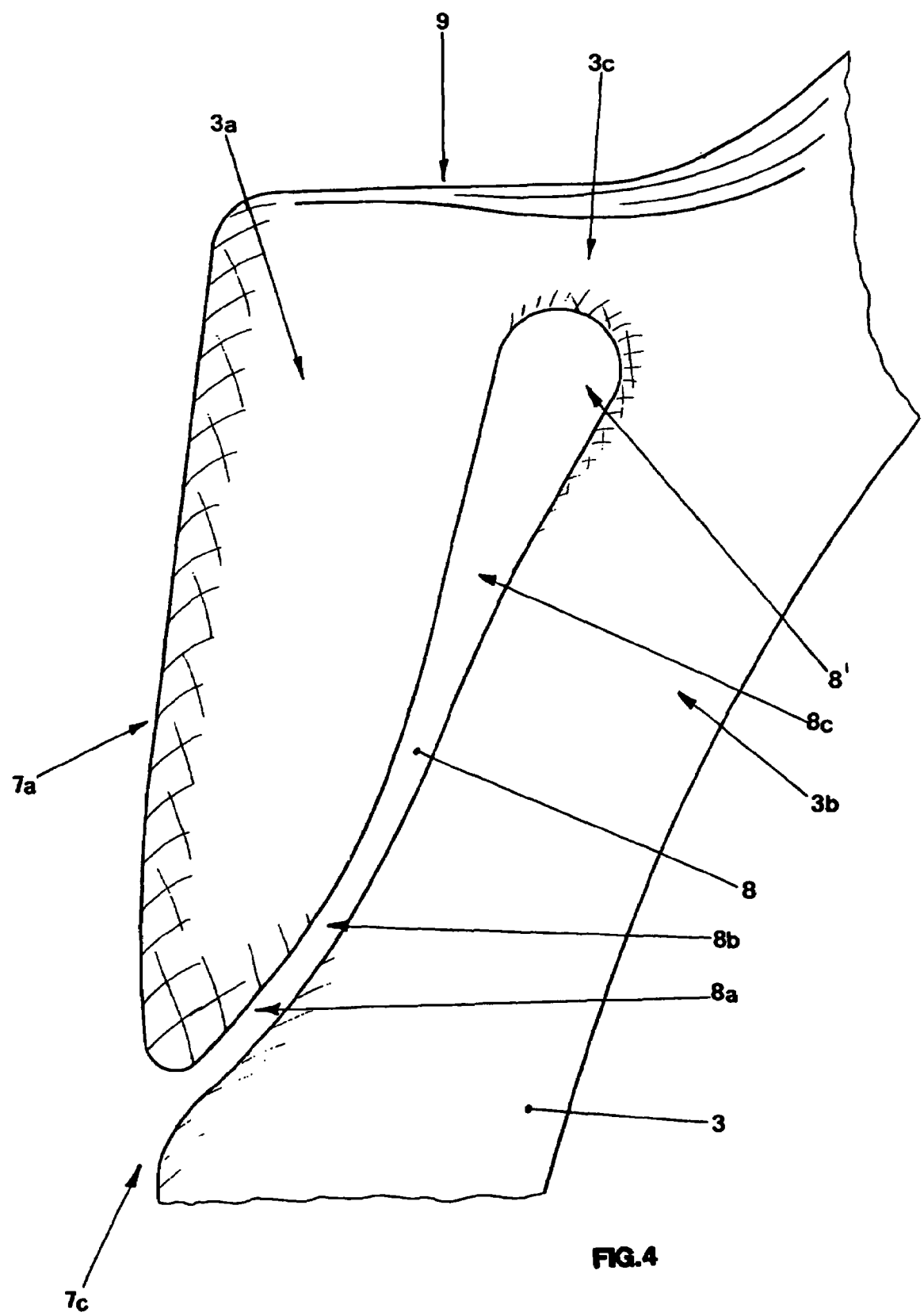
FIG. 4 is an enlarged detail of the stem of FIG. 3.

The shaped notch 8 whose shape comes from tests with finite elements method, consists of a concave-convex continuous surface 8a defining a profile 8' generally having a shape of a half slot as shown in FIG. 4.

More particularly the profile 8' is preferably but not necessarily constituted by a first stretch 8b connected to the mixtilinear surface 7 with a generally constant cross section and a second stretch 8c extending until under the bridge 7c with a widened crossed section.

Figure 5:
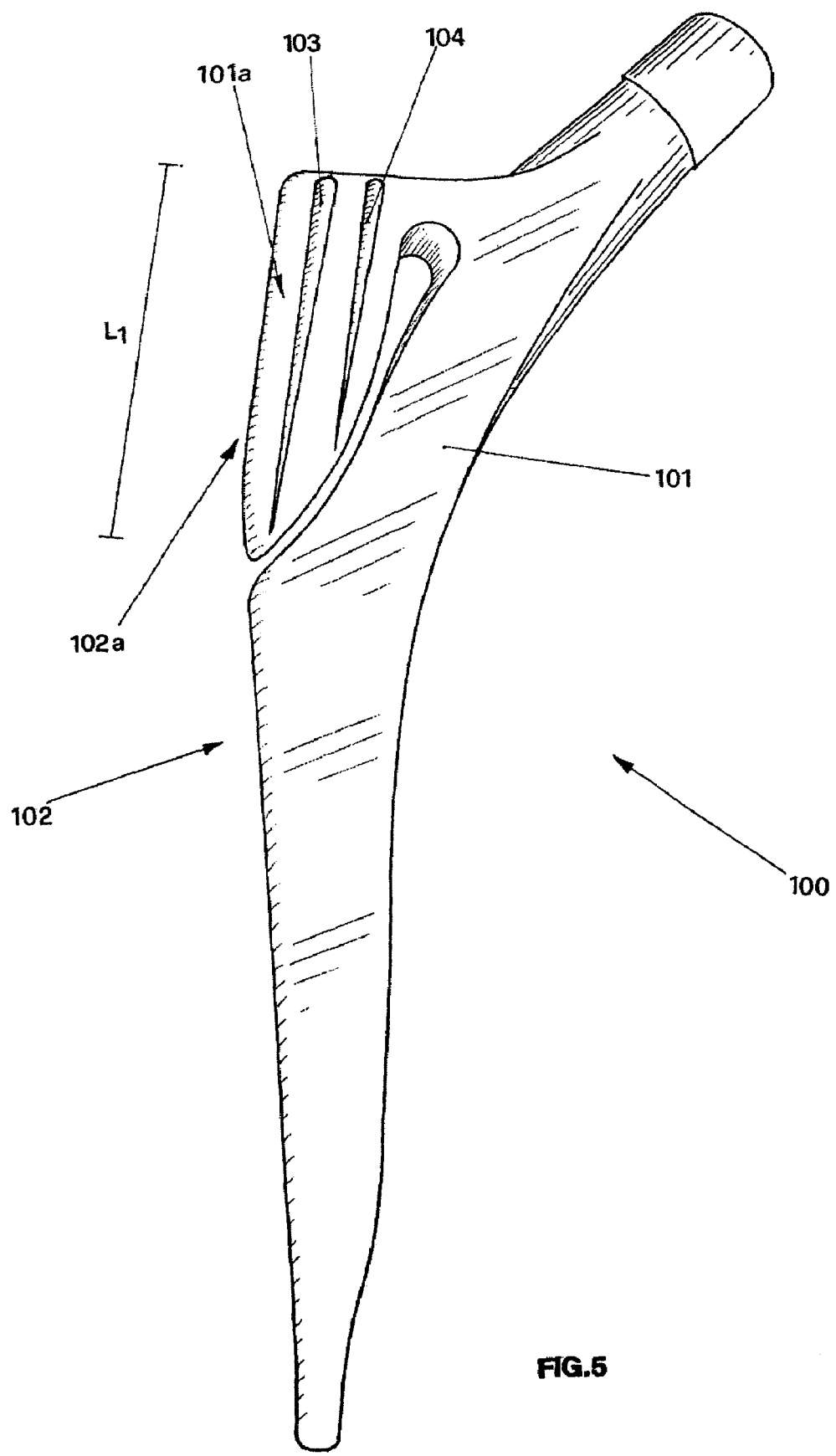
FIG. 5 is an executive variation of the femoral stem of FIG. 3.

FIG. 5 shows an executive variation of the femoral stem of the invention now generally indicated with 100, which is different from the preceding embodiment because the first zone 101a of the central body 101 is provided with an outer couple of longitudinal fins indicated with 103 and 104 respectively, extending generally for the entire length $L_1$ of the first zone 101a.

Figure 6:
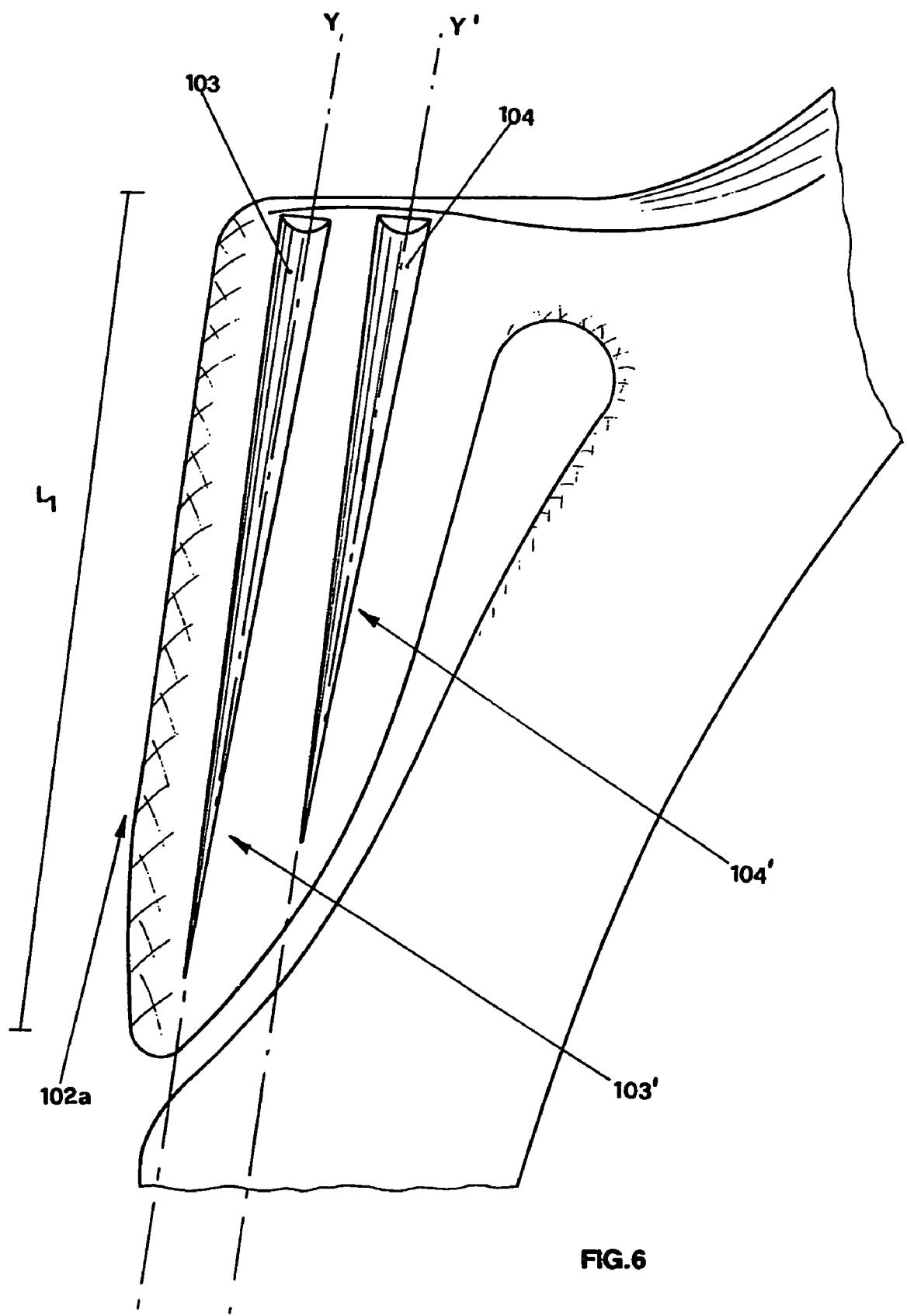
FIG. 6 is an enlarged detail of the stem of FIG. 5.

As shown in FIG. 6 according to the preferred embodiment now described the longitudinal fins 103, 104 have a cross sectional conical profile 103', 104' and are arranged along corresponding longitudinal axis Y, Y' parallel to each other and generally parallel to the first surface 102a of the mixtilinear surface 102 defining the central body 101 from one side.

It is clear that according to another executive variation, the first zone of the central body may comprise any number of longitudinal fins as a function of the dimensions of said central body depending in turn by the configuration of the femur in which the femoral stem is being inserted.

Such longitudinal fins have the purpose to enhance the bone integration stimulating the spongy bone with which they enter exclusively in contact in view of their arrangement on the stem without damaging it to much thanks to their rounded profile.

Moreover their development line is rather advantageous when the stem 100 is inserted in the femur F with a curved path defining the type of insertion known in the art as banana insertion, which is not coincident with the vertical direction parallel to the axis Z' of the femur F.

This insertion method well known in the surgery methods, allows a further bone saving in the zone adjacent to the greater trochanter G.

During this kind of operations, the longitudinal fins 103, 104 remain always tangent to the curved path of insertion of the femoral stem 100 into the femur F.

In this way the fins do not rub and remove spongy bone J so as not to create a marked hollow zone between the femoral stem 100 and the femoral bone F which would be hard to fill with time by the natural process of bone integration as it occurs however with the femoral stems of the prior art.

This latter stems are indeed provided with outer longitudinal fins that in surgical operations of banana insertion of the stem into the femur, cancel the object for which they were provided, namely to allow a better anchorage of the femur to the stem, because said fins are arranged along a vertical direction generally parallel to the main development direction of the stem.

Operatively the surgery of application of the prosthesis are to the hip A of the patient, more particularly of the femoral stem 1 of the invention, consists initially in reception of the head T of femur F and the subsequent preparation by proper rasps of the femoral canal N.

To obtain the most possible advantages of the invention, the seat of the femoral stem 1 is advantageously obtained in some zones without removing the spongy bone J as it occurs in most surgical methods now used in orthopedic surgery but pressing it against the cortical bone K.

This allows to stimulate equally the cortical bone K making it reactive and therefore adapted to grow and strengthen besides keeping the spongy bone J enhancing the ability of bone integration to the femoral stem.

It is also known that even a partial saving of removal of spongy bone decreases the blood loss and makes the post operative recovery of the patient easier.

The surgery continues with removal of the zone comprised between the greater trocanter G and the neck L already removed, to allow insertion of the femoral stem 1 into the femoral canal N of femur F indifferently along a vertical direction or curved path.

Then one proceeds to the application of the spherical head S to the terminal pin 5 of the femoral stem 1 thus allowing the joint with cotyle I previously applied to the acetabular zone E and completing the assembly of prosthesis R of the hip A.

Under load conditions, the second zone 3a of the central body 3 bends downwards thus stimulating the zone of femur F facing it, more particularly the calcar subject to degeneration with femoral stems of the prior art because it is not sufficiently stimulated.

Thanks to the shaped notch 8 making the femoral stem 1 less inert, under load conditions even the first zone 3a of the central body 3 is pulled downwards thus stimulating advantageously the greater trochanter G.

Therefore the femoral stem 1 as much as possible being of metal material, results to be less rigid in comparison with equivalent stems of the prior art, still not compromising its primary and secondary stability indispensable for the correct anchorage and integration with femur F.

As a matter of fact, the peculiar characteristics of the femoral stem of the invention are those to be provided with a certain degree of elasticity making it more integral with the femur to stimulate the crucial parts and at the same time not to hinder or compromise the process of anchorage and bone integration to the stem because of an incorrect and excessive mobility inside the femur.

It is clear that these aspects confer to the femoral stem of the invention an absolute level of peculiarity and efficiency that cannot be reached with the stems of the prior art.

On the basis of the foregoing it is therefore understood that the femoral stem of the invention attains all the previously mentioned objects and advantages.

In the executive stage modifications made be made to the femoral stem of the invention for example consisting in a different profile of the shaped notch.

In addition even the surfaces defining the femoral stem may have a different shape from the above described one, without impairing the advantage given by the present invention.

All the variations described and cited but not illustrated in the accompanying sheets of drawings, when falling in the scope of the appended claims, should be considered protected by the present patent.

The invention claimed is:

1. A femoral stem for hip prosthesis, comprising:
   a main body with mainly longitudinal development and with a generally wedge shape, adapted to be inserted into the femoral canal present in a body of a femur;
   a central body of a generally trapezoidal shape integral with said main body, adapted to be located in a proximal zone of said femur; and
   an appendix projecting from said central body, provided with a terminal pin adapted to receive a spherical head of a joint in a cotyle belonging to said prosthesis and inserted in an acetabular zone of a pelvic bone,
   wherein said main body and said central body are defined by a shaped surface on a medial side of the femoral stem and by a surface having a mixtilinear profile on an opposite lateral side,
   wherein said central body includes a shaped notch in the form of an open-ended slot, wherein the shaped notch is a solitary notch, wherein said notch,
   wherein said notch includes an open end at the mixtilinear profile of said main body and extends generally toward the projecting appendix, said shaped notch passing through a thickness of said central body from an anterior side to a posterior side of the femoral stem,
   wherein the central body includes a first zone, arranged generally to face a greater trochanter of said femur, and a second zone, arranged generally to face a lesser trochanter of said femur, and
   wherein said first zone and said second zone are joined at a bridge portion disposed adjacent a closed end of the notch at the posterior side of the femoral stem.

2. The femoral stem according to claim 1, wherein said shaped notch has a smooth concave-convex continuous inner surface defining.

3. The femoral stem according to claim 1, wherein said mixtilinear profile consists of a first generally straight profile at said central body, and a second generally straight profile at said main body approaching said first profile at the opening of said shaped notch.

4. The femoral stem according to claim 1, wherein the first and second zones are connected only at the bridge, and are otherwise completely separated by the shaped notch.

5. The femoral stem according to claim 3, wherein an extension of said second profile in the direction of the first profile defines with said first profile an acute angle.

6. The femoral stem according to claim 2, wherein said inner surface of said shaped notch has a profile that consists of a first portion beginning at the opening of the notch having a generally constant cross section, and a second portion continuing from the first portion and extending until below said bridge, having a widened cross section.

7. The femoral stem according to claim 1, wherein said first zone of said central body includes at least one external longitudinal fin generally extending for the entire length of said first zone.

8. The femoral stem according to claim 7, wherein said at least one fin is arranged along a longitudinal axis generally parallel to said first profile of said mixtilinear profile.

9. The femoral stem according to claim 7, wherein said at least one fin has a cross sectional conical profile.

10. The femoral stem according to claim 1, wherein said shaped surface has a concave-convex profile in longitudinal section.

* * * * *